(12) United States Patent
Guirguis

(10) Patent No.: US 6,423,237 B1
(45) Date of Patent: *Jul. 23, 2002

(54) METHOD AND APPARATUS FOR MANUALLY SEPARATING PARTICULATE MATTER FROM A LIQUID SPECIMEN

(75) Inventor: Raouf A. Guirguis, Vienna, VA (US)

(73) Assignee: LaMina, Inc., Arlington, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/963,873

(22) Filed: Nov. 4, 1997

Related U.S. Application Data

(60) Continuation-in-part of application No. 08/905,833, filed on Aug. 14, 1997, now Pat. No. 6,106,483, which is a continuation of application No. 08/474,894, filed on Jun. 7, 1995, now abandoned, which is a division of application No. 08/172,232, filed on Dec. 23, 1993, now Pat. No. 5,471,994, which is a division of application No. 07/920,662, filed on Jul. 28, 1992, now Pat. No. 5,301,685.

(60) Provisional application No. 60/054,799, filed on Aug. 5, 1997.

(51) Int. Cl.$^7$ ............................................... B01D 43/00
(52) U.S. Cl. ................. 210/767; 210/768; 210/808; 210/416.1; 210/437; 210/451; 210/455; 210/474; 210/477; 422/99; 422/101; 422/102
(58) Field of Search .................. 210/645, 451, 210/455, 359, 474, 416.1, 416.3, 453, 767–768, 780–782, 413, 459, 460, 477, 435, 437, 808; 600/573, 584; 422/99, 101, 102

(56) References Cited

U.S. PATENT DOCUMENTS 3,481,477 A * 12/1969 Farr
3,870,639 A * 3/1975 Moore et al. ............... 210/359
3,955,423 A * 5/1976 Ohringer
3,983,037 A * 9/1976 Lee et al. .................... 210/416
4,430,213 A * 2/1984 Ishikawa .................... 210/136
4,685,472 A * 8/1987 Muto
5,282,978 A * 2/1994 Polk, Jr. et al. ............ 210/767
5,301,685 A * 4/1994 Guirguis
5,422,273 A   6/1995 Garrison et al. ........... 435/296
5,429,803 A * 7/1995 Guirguis
5,471,994 A * 12/1995 Guirguis
5,624,554 A   4/1997 Faulkner et al. ........... 210/232
5,849,505 A * 12/1998 Guirguis
6,296,764 B1 * 10/2001 Guirguis .................. 210/323.1

FOREIGN PATENT DOCUMENTS

| EP | 0 448 837 A | 10/1991 |
| EP | 0 471 570 A | 2/1992 |
| EP | 0 483 506 A | 5/1992 |
| FR | 2 691 977 A | 12/1993 |
| WO | WO 94 03103 | 2/1994 |

* cited by examiner

Primary Examiner—Matthew O. Savage
Assistant Examiner—Marianne S. Ocampo
(74) Attorney, Agent, or Firm—Foley & Lardner

(57) ABSTRACT

An apparatus and a method for separating particulate matter from a fluid, wherein the apparatus includes a specimen container, a porous arrangement positioned in a housing and suitable for collecting particulate matter in the liquid on a collection site, and a pump. The housing includes a first portion having elements that improve fluid flow through the housing and elements that decrease the porous arrangement retention characteristics of the portion. The housing also includes a portion having elements that increase the porous arrangement retention characteristics of the portion.

32 Claims, 7 Drawing Sheets

METHOD AND APPARATUS FOR MANUALLY SEPARATING PARTICULATE MATTER FROM A LIQUID SPECIMEN

CROSS-REFERENCE TO RELATED APPLICATIONS

This application claims the benefit of U.S. provisional application Serial No. 60/054,799 (filed Aug. 5, 1997), and is a continuation-in-part of U.S. application Ser. No. 08/905,833 filed on Aug. 14, 1997 (now U.S. Pat. No. 6,106,483), which is a continuation of U.S. application Ser. No. 08/474,894 filed on Jun. 7, 1995 (now abandoned); which is a divisional of U.S. application Ser. No. 08/172,232 filed on Dec. 23, 1993 (now U.S. Pat. No. 5,471,994); which is a divisional of U.S. application Ser. No. 07/920,662 filed Jul. 28, 1992 (now U.S. Pat. No. 5,301,685).

TECHNICAL FIELD OF THE INVENTION

The present invention is directed to an improved apparatus and method for collecting a uniform layer of cells from body fluids suitable for use in improved cytological protocols.

BACKGROUND OF THE INVENTION

In a wide variety of technologies, the ability and/or facility in separating matter, typically particulate matter, from a fluid is a critical component in the ability to test for the presence of substances in the fluid. Too often, interference associated with sample preparation obscures the target cells to such a degree that the process is not sufficiently reliable, or too costly.

A similar scenario applies to many other fields which involve detection and/or diagnosis, including environmental testing, radiation research, cancer screening, cytological examination, microbiological testing, and hazardous waste contamination, to name just a few.

In all of these endeavors, a limiting factor in the sample preparation protocol is adequately separating solid matter from its fluid carrier (e.g., a variety of fluids, such as physiological, biological and environmental), and in easily and efficiently collecting and concentrating the solid matter in a form readily accessible to microscopic examination.

Prompt processing of urine to obtain fresh cells traditionally has been recommended to ensure the accuracy of quantitative culture results, urinalysis and microscopy. Fresh cells tend to stick to a glass slide much better than cells from preserved urine, allowing for smoother cell spread onto the glass body. Delays in processing, negligent care in either inpatient or outpatient settings and lack of refrigeration may lead to non-optimal slide preparation. One known solution to the delay problem is the use of chemical preservatives with the urine. The presence of liquid preservatives, however, in the urine specimen raises the specific gravity of the specimen to unmeasurable levels and may limit the potential usefulness of the urine for various types of traditional quantitative analysis, such as slide microscopy.

A number of urine or other biological fluid specimen containers have been developed to allow liquid biological specimens to be tested without removing the lid of the urine or biological fluid container. None of the prior art solves the problem of transferring cells in a uniform layer to a slide for examination while at the same time preserving the fluid from which the cells were taken.

Currently, body fluid samples are collected for cytological examinations using special containers. These containers usually contain a preservative solution for preserving the cytology specimen during shipment from the collection site to the cytology laboratory. Furthermore, cytology specimens collected from the body cavities using a swab, smear, flush or brush are also preserved in special containers with fixatives (e.g., alcohol or acetone fixatives) prior to transferring cells onto the slide or membrane for staining or examination.

Diagnostic microbiology and/or cytology, particularly in the area of clinical pathology, bases diagnoses on a microscopic examination of cells and other microscopic analyses. The accuracy of the diagnosis and the preparation of optimally interpretable specimens typically depends upon adequate sample preparation. New methodologies such as immunocytochemistry and image analysis require preparations that are reproducible, fast, biohazard-free and inexpensive. Different cell preparation techniques of the present invention address the issues of non-uniform cell densities, uneven cell distribution and air drying artifact. These preparations have resulted in an even distribution of cells that have superior morphology, which has improved light microscopic visualization and has allowed for the use of image cytometry instruments.

The solid matter preparation techniques of the present invention address the issues of non-uniform matter densities, uneven matter distribution, and sample loss due to the number of steps involved in the sample preparation. The preparations of the present invention result in an even distribution of solids that have superior morphology, improved visualization, and are readily positioned and available for light absorbance analysis without the need to further manipulate or prepare the sample.

SUMMARY OF THE INVENTION

The present invention relates to an apparatus and method for collecting matter for detection, analysis, quantification, and/or visualization. The devices and methods of the present invention are particularly suitable for separating matter from biological, physiological, and environmental fluids and presenting the particulate matter in an improved manner for cytological examination.

The present invention relates to an apparatus and method for collecting a uniform layer of cells from urine or other biological fluid specimen in a cytology collection apparatus or assay module, which can be removably detached from a specimen container for application to a slide. The separate container may be sealed by the patient or medical person handling the collection. The collection of the cells in the cytology collection apparatus allows a uniform cell slide to be obtained without contamination of the cells by preservatives, workers or outside materials. The transfer from collection container to the cytology collection apparatus may be carried out without pouring or pipetting the collected specimen.

The present invention is directed to a cell collection and distribution apparatus which can be disassembled to allow face to face transfer of cells from the device to a slide for microscope examination. The present invention provides an improved apparatus and method for collecting a monolayer of cells which can be transferred to a microscope slide.

The devices of the present invention obviate the need for a trained technician to properly prepare a sample substrate. Thus, time, expense, and expertise are eliminated or reduced as critical factors in sample preparation protocols.

The devices and methods of the present invention also provide advantages in sample preparation because they are suitable for use with fresh, untreated cells, unmodified cells, and are particularly designed to provide a thin, uniform layer of solid matter (up to approximately 40 microns or more). This invention is particularly useful for collecting cells for a pap smear.

The present invention is also directed to a cytology collection and testing kit containing the cytology collection apparatus described above. The cytology collection kit may also include replacement filters, replacement disposables, and/or other components or solutions typically used during cytological examinations.

According to another aspect of the present invention, the matter collection apparatus may also include additional modules, removable or integrated, for treating the fluid. For example, the fluid may be treated with a matter collection module, in combination with a debris removal module, a chromatography module, an assay module, or combinations of these and other devices. These and other modules or treatment protocols provide features which may be desirable to incorporate into a sample preparation apparatus according to the invention.

For example, the devices and methods of the present invention have many advantages for conventional microbiology and hematology. The collected cells are in a predetermined area easily accessible to a radiant light source and to a wavelength absorbance meter. Because cells are concentrated in a single layer, they are almost always in one focal plane, thus eliminating or reducing interference by other particles and virtually eliminating technician time and expertise in establishing a proper reading. The minimal matter overlap achieved ensures that all matter can be easily examined with little chance for critical solids to be obscured by clumps of overlapping solids or debris. The apparatuses of the present invention even permit the use of automated devices to detect and analyze any solid matter in a given population. It also permits a detailed analysis of the chemical composition of the matter.

The effectiveness of transferring the monolayer cells from the filter to a microscope slide has proven to be very high without differential cell loss. Microscopic examination shows that the cell distribution is the same on the slide as on the filter.

The devices and methods of the present invention have many advantages for conventional cytology. The cells are in a predetermined area allowing for significant timesaving when screening the slide. Such problems as cells lying outside the coverslip or on the frosted end are eliminated. Because cells are lying in a single layer, they are almost always in a one focal plane when using a 10× objective—the objective most often used for the lower power screening of a slide. Even with a 40×objective, most cells are in focus. This eliminates frequent refocusing and saves time.

The accompanying drawings show illustrative embodiments of the invention from which these and other of the objectives, novel features and advantages will be readily apparent.

DETAILED DESCRIPTION OF THE INVENTION

Figure 1:
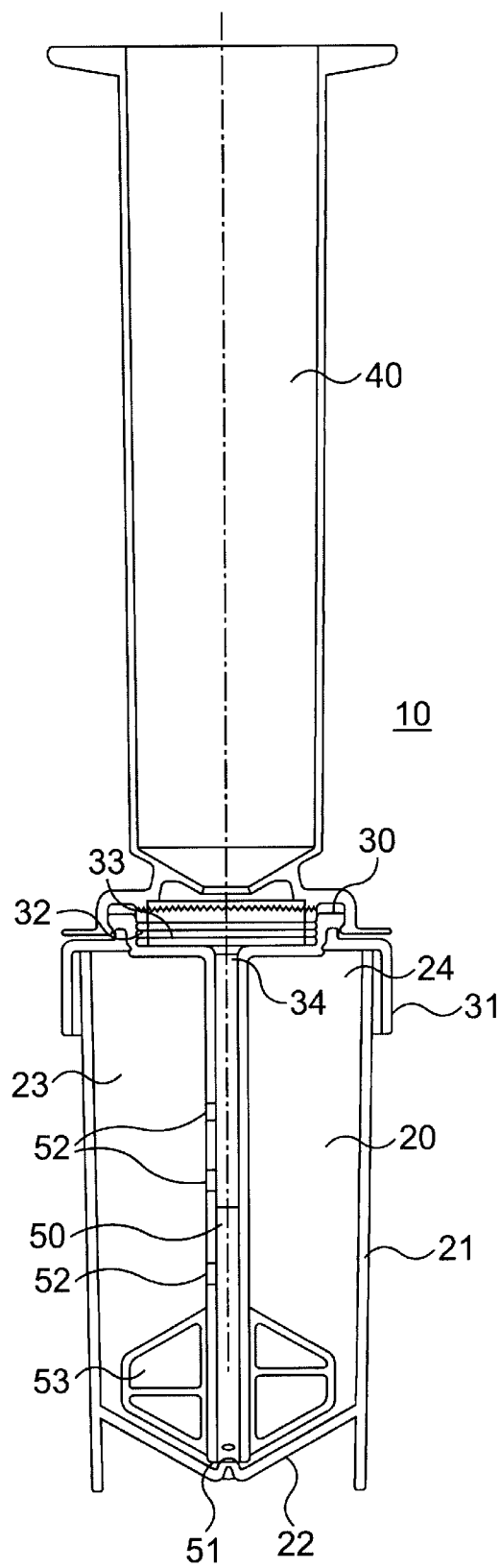
FIG. 1 is a cross section view of an embodiment of the invention.

The present invention comprises a specimen container that includes a particulate matter separation housing or module in fluid communication with a specimen container.

The present invention is also a device for processing a fluid into one or more components, typically by removing particulate matter from the fluid.

The present invention also includes devices and methods for collecting fluids, such as biological, physiological, or environmental fluids, removing the desired matter from the fluid, without centrifugation, and diagnosing and testing the matter. In a preferred embodiment of the invention, particulate matter is collected on a collection site. In a most preferred embodiment of the invention, the particulate matter is collected in a monolayer and in a predetermined spatial arrangement.

The present invention also includes an improved apparatus and method for processing a fluid containing particulate matter. The apparatus and method include passing the fluid through a chamber having a seat for a porous arrangement, said seat including structures for aligning the collected particulate matter in a pre-determined spatial arrangement, structures that enhance the fluid flow through the chamber, and/or structures that promote or retain the porosity and/or compression of the porous arrangement housed in the chamber.

The present invention is also an improved device for collecting and processing a fluid, typically a biological fluid, the device including a particulate matter separation housing having one or more of the following: a porous arrangement chamber; a membrane for separating particulate matter from a liquid; a porous support; a porous arrangement that establishes at least two fluid flow paths through the chamber; a porous arrangement seat that configures the collected particulate matter in a predetermined pattern; a concentric channel in the chamber; a channel having one or more resilient members; a chamber seat having one or more resilient members; a chamber seat or base having posts; a chamber seat having one or more predetermined surface modifications; a seat having one or more elements that promote a predetermined spatial arrangement of particulate matter on a collection site; and structures that enhance the fluid flow through the chamber.

A device according to the present invention may also include structures that are configured for and/or are adapted to mix the specimen collected in the specimen container. Exemplary structures include but are not limited to a specimen container having a rotatable cover, or a portion of the cover that rotates; a cover or cover portion that is moveable in relation to the specimen container; and a tube or the like that extends into the specimen container, said tube including one or more elements that mix the specimen. The cover may also include a portion that fittingly engages a portion of the cover in a liquid-tight seal. The cover may also include a portion that fittingly engages a portion of the cover in a liquid-tight but not fluid-tight seal.

A device according to the invention may also include a pump or syringe portion, said portion optionally including one or more elements configured to permit a predetermined amount of fluid into the pump or syringe.

The present invention also includes preparing a fluid for microscopic examination by processing a fluid using a device according to the invention, and collecting particulate matter on a collection site in the device.

The present invention also includes a method for analyzing matter comprising collecting a sample in a specimen container, collecting matter on a collection element, and transferring the matter collected on the collection element to a microscope slide or the like. Preferably, both collecting steps occur within the same apparatus.

A device according to the invention may also include one or more separable elements. In a preferred embodiment of the invention, the device includes a separable particulate matter separation housing. In a most preferred embodiment of the invention, the device includes a particulate matter separation housing having an upper portion of the housing configured to retain at least a portion of a porous arrangement.

The present invention also includes a kit having an assay module which includes a matter collection element according to the invention, a fluid specimen container, and a pump for inducing fluid flow through the assay module.

In a preferred embodiment of the invention, a specimen container includes a chamber for collecting a liquid specimen, and in fluid communication with the chamber, a particulate matter separation housing or module for separating particulate matter in the fluid and collecting the separated particulate matter at a collection site. In a most preferred embodiment of the invention, the separated particulate matter is collected in a monolayer at the collection site. A preferred embodiment of the invention also includes a hollow tube in fluid communication with the particulate matter separation housing. More preferably, the hollow tube includes means for mixing the specimen and/or dispersing the particulate matter in the specimen.

In another embodiment of the invention, the apparatus includes the specimen container and particulate matter separation housing described above, and a pump or syringe or the like. In this embodiment of the invention, the various structures provide a fluid flow path from the specimen container, through the particulate matter separation housing, and into the syringe.

As used herein, fluid refers to any fluid for which it may be desirable to collect a component of the fluid for the purpose of establishing its identity or presence in the fluid. Typically, the component in the fluid will be a solid matter, such as particulate matter. For example, the fluid may be air or gas, or a biological fluid, such as urine, and it may be desirable to determine the presence of cancer cells or certain proteins in the biological fluid. In another example, it may be desirable to evaluate the nature of contaminants, such as molecular contaminants, in ultra-pure water used in the electronics industry. Other exemplary fluids include but are not limited to body fluids, such as blood, spinal fluid, or amniotic fluid; bronchial lavage; sputum; fine needle aspirates; ground water; industrial processing fluids; electronic or medical dialysis fluids; to identify just a few. It is intended that the invention should not be limited by the type of fluid being processed.

As used herein, particulate matter refers to any substance in a fluid which is capable of collection and evaluation, preferably by cytological examination. Exemplary particulate matter includes, but is not limited to cells or cell fragments, proteins, molecules, polymers, rubbers, stabilizers, antioxidants, accelerators, silicones, alkyds, thiokols, paraffins, thermoplastics, bacteria, pesticides, and herbicides. Specific exemplary polymeric matter include, but is not limited to polyethylene, polypropylene, polyisobutylene, polyacrylonitrile, polyethylene glycol, polyvinylchloride, polystyrene, polysulfide, polymethylmethacrylates, polyethyleneterephthalates, bisphenol A (a common environmental contaminant), ethyl cellulose, nitrocellulose, polyurethane, and nylon. Specific exemplary biological matter includes cancer cells, including distinguishing between metastatic and normal cancer cells; proteins, nucleic acids, antibodies, or the like. While a cytology collection apparatus according to the invention can be used for any biological fluid, it is particularly useful for preparing testing samples from urine and its associated cells for Pap smears. The most widely used stain for visualization of cellular changes in cytology is the Papanicolaou staining procedure. This stain, which is used for both gynecologic and non-gynecologic applications, is basically composed of blue nuclear and orange, red and green cytoplasmic counterstains. The nuclear stain demonstrates the chromatic patterns associated with normal and abnormal cells, while the cytoplasmic stains help to indicate cell origin. The success of this procedure can be attributed to the ability to observe a number of factors, including definition of nuclear detail and cell differentiation. This staining procedure also results in a multicolor preparation that is very pleasing to the eye, possibly reducing eye strain.

It is intended that the invention should not be limited by the type of matter being processed. In a most preferred embodiment of the invention, the fluid is urine and the particulate matter is a cell.

The particulate matter processing apparatus 10 of the present invention also permits isolation and collection of fresh cells and/or microorganisms from biological fluids to perform DNA probe and chromosomal analysis once the cells are hemolyzed by the proper buffer.

As used herein, adapted for communication, communicating, or similar terms refer to any means, structures, or methods for establishing fluid flow through the system, as are well known by practitioners in the art. Exemplary structures are shown in the Figures. For example, a conduit may have a connector adapted to receive or connect to a mated connector on another conduit. As used herein, connector refers to any structure used to form a joint or to join itself to another piece. These connectors or connections establish a fluid flow path through various elements of the apparatus, assembly, or system. Typical connections include but are not limited to mating connections, such as Luer-type, screw-type, friction-type, or connectors that are bonded together.

The present invention, an exemplary embodiment of which is shown in FIG. 1, includes a specimen container 20 defining a collection chamber 23, a particulate matter separation housing 30 defining a porous arrangement chamber, and a pump 40. FIG. 1 also shows hollow tube 50 in the embodiment of the invention that includes dispersing elements (fins) 53.

Each of these elements will now be described in more detail.

The Specimen Container

In accordance with the invention, specimen container 20 includes any container suitable for holding a fluid, preferably a biological fluid. The typical container includes side walls 21 and bottom wall 22 that, in combination, provide a chamber 23 having an open end 24 for collecting, holding, or storing a fluid. Typical fluids include, but are not limited to biological fluids, such as body fluids, waste water fluids, or the like. Typical body fluids include urine or other biological fluids, such as blood, cerebrospinal fluid (CSF), bronchial lavage, sputum or fine needle aspirates.

The configuration and materials used to make the container (and any of the elements that comprise a device according to the invention) can be any of a variety of materials, shapes, and sizes. For example, the container can be constructed of any material compatible with the fluid to be processed. It will be appreciated that the container and the assembly of the side walls to the bottom wall can be any conventional assembly. In a preferred embodiment of the invention, bottom wall 22 is a conical member, as shown in FIG. 1. Optionally, bottom wall 22 or side wall 21 may include one or more fins or the like (not shown) extending into the chamber. Such fins may be desirable an embodiment of the invention described in more detail below in which the sample in the container is mixed by rotation of the container.

Figure 2:
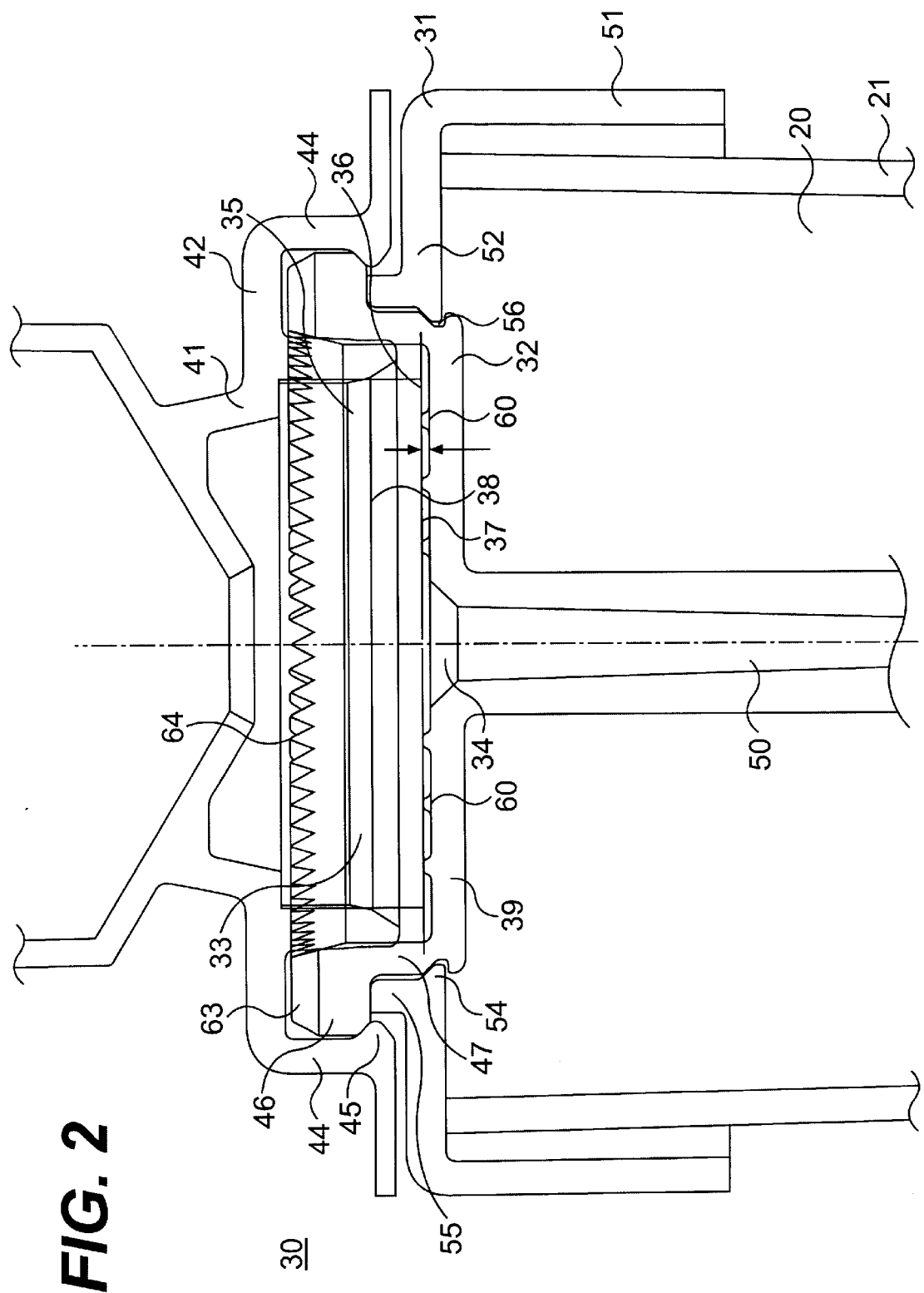
FIG. 2 is a cross section view of the particulate matter separation housing.

As shown in FIGS. 1 and 2, a device according to the invention also includes a cover or lid 31. In a preferred embodiment of the invention, the cover is configured or adapted to receive a lower portion 32 of a particulate matter separation housing 30. The cover may be variously configured to achieve the desired function. A typical configuration is shown in FIG. 2. The cover 31 may include a downwardly extending member 51 configured to engage side wall 21 of container 20. It is intended that cover 31 may be any configuration or shape that closes or seals open end 24 of container 20.

The cover 31 also includes portion 52 having an opening defined by projection 54 adapted to receive the lower portion 32 of the particulate matter separation housing. Although the engagement between portion 52 and lower portion 32 may be variously configured, lower portion 32 preferably includes a groove 56 adapted to receive projection 54 in cover portion 52. In a most preferred embodiment of the invention, the engagement is a snap fit, with the engagement between housing lower portion 32 and the projection 54 permitting housing lower portion 32 to rotate. This configuration is preferably liquid tight, and in a most preferred embodiment of the invention, the seal is liquid tight but not fluid (e.g., air) tight.

An alternative or additional structure in the embodiment of the invention that includes a cover with a moveable element is a wall 55, preferably circular or elliptical, that engages and/or supports a portion of the particulate matter separation housing 30. In a most preferred embodiment of the invention, the wall 55 includes one or more spaced apart notches. It is intended that these notches provide a degree of flexibility in the wall 55 so that, if desired, the lower portion 32 of the particulate matter separation housing can be disengaged from the cover and/or moveable portion of the cover (see, for example, FIG. 5).

Particulate Matter Separation Housing

In accordance with the present invention, a device according to the invention includes a particulate matter separation housing that may be variously configured. An exemplary configuration is shown in FIG. 2. Any housing 30 adapted to receive a particulate matter collection assembly 33 may be used. Particulate matter collection assembly 33 includes a porous arrangement 35 having a collection site 36.

As shown in FIGS. 1 and 2 the particulate matter separation housing 30 is preferably a two piece housing formed by an upper portion 41 and lower portion 32. In a preferred embodiment of the invention, upper portion 41 releasably engages lower portion 32; any housing configuration or assembly providing access to the porous arrangement 35 is suitable. In a preferred embodiment of the invention, lower portion 32 includes a side wall 47, typically circular, that optionally includes a serrated portion 63 (shown in FIG. 4) that engages or communicates with side wall 44 and seat 42 of upper portion 41. It has been found that the optional serrated portion 63 of lower portion 32 facilitates disengaging the lower portion 32 from the upper portion 41. Upper portion 41 and lower portion 32 may be connected or fastened to each other by any mating connection or means that provides a liquid or fluid tight fit, e.g., Luer-type (threaded or not threaded), screw thread-type, friction-type, a tapered mating connection, or snap fit (as illustrated).

Lower portion 32 includes a side wall and bottom wall suitable for seating a particulate matter collection assembly 33. Lower portion 32 may also include a central bore or aperture 34 communicating with a hollow tube 50. In a preferred embodiment of the invention, hollow tube 50 extends into specimen container 20. In a preferred embodiment of the invention, lower portion 32 may be a separate structure that is capable of rotating in the cover 31. In order to achieve ease of centrifugal rotation while maintaining a liquid-tight assembly, lower portion 32 may matingly engage cover 31 through a tongue and groove arrangement 54, 56 (see FIG. 2) which permits unlimited rotation of the lower portion 32 relative to the cover 31.

Figure 4:
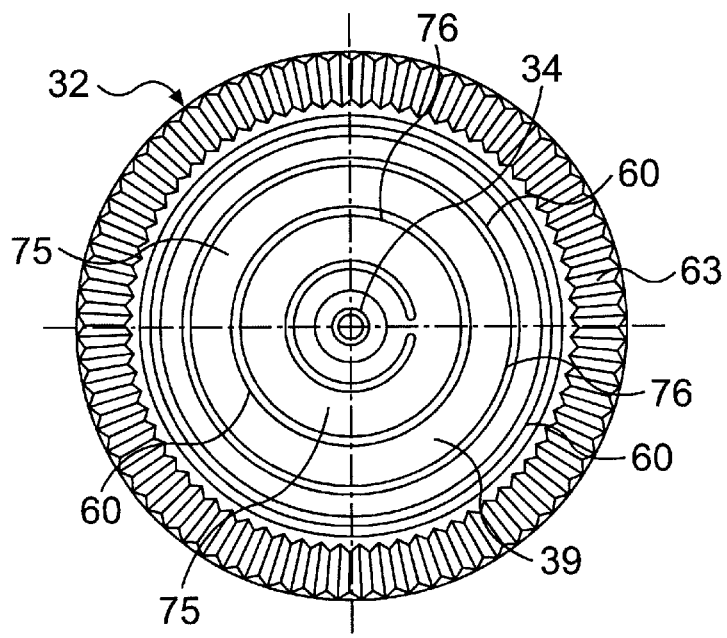
FIG. 4 is a top view of the lower portion of the particulate matter separation housing.
Figure 6:
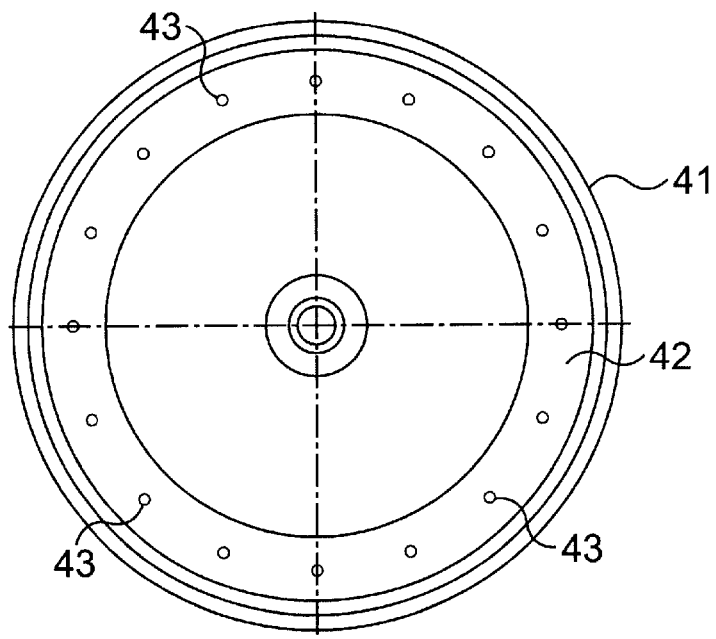
FIG. 6 is a bottom view of the upper portion of the particulate matter separation housing.

In accordance with an embodiment of the invention, lower portion 32 of the particulate matter separation housing includes a bottom wall or seat 39. As shown in FIGS. 2 and 4, seat 39 may include one or more spaced apart ribs or projections 60. Projections 60 are preferably of a configuration, size, and shape sufficient to prevent porous arrangement 35 from flushly contacting seat 39. In the embodiment shown in FIG. 4, projections 60 are concentric rings.

Alternative configurations are described in more detail below. In a preferred embodiment of the invention, projections 60 function in one or more of the following ways: projections 60 may break the surface tension between porous arrangement 35 and seat 39 so that, during use, when porous arrangement 35 is pulled away from seat 39, first porous medium 37 does not remain in contact with seat 39; projections 60 may evenly distribute pressure of the porous arrangement in the housing; projections 60 may prevent or suppress compression of the porous arrangement; and projections 60 may be configured to distribute any collected particulate matter in a predetermined configuration or spatial distribution.

In accordance with the present invention, the surface of seat 39 may include one or more structures, configurations, or surface textures that promote the ability of the porous arrangement 35 to release from the seat, that promote a pre-determined spatial distribution of particulate matter on the collection site, and/or prevent or suppress compression of the porous arrangement. One embodiment of the invention includes concentric projections, such as projections 60 described above. Other configurations include, but are not limited to a grid, cross-hatching or the like, concentric squares or rectangles, or a series of continuous or separated structures, nubs, protuberances, granulations, or the like. It is intended that any element, structure, or chemistry that provides a texture to the surface of the seat 39 is suitable for use with the present invention.

Figure 8:
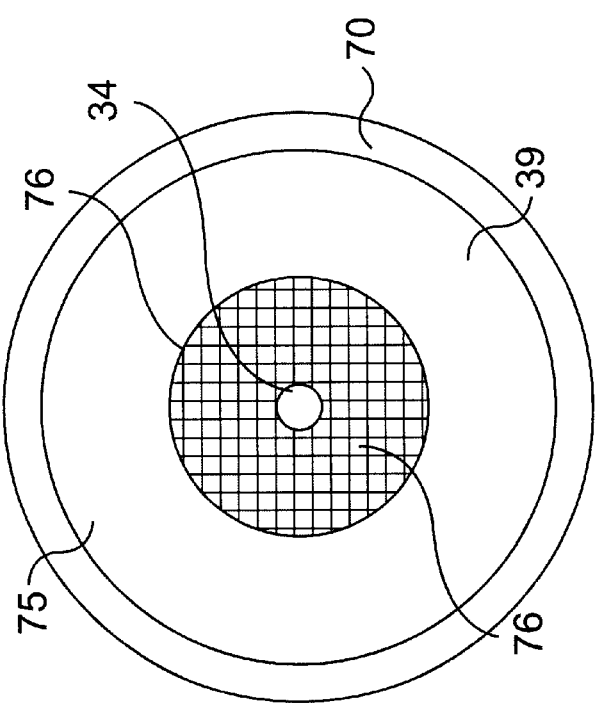
FIG. 8 is a top view of the lower portion of the particulate matter separation housing, and illustrates a cross hatch face surface modification of the seat.
Figure 7:
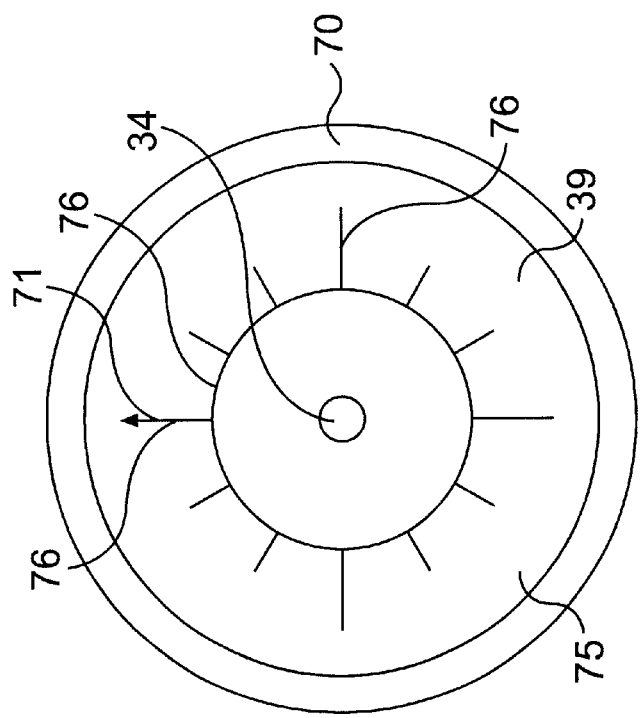
FIG. 7 is a top view of the lower portion of the particulate matter separation housing, and illustrates a clock face surface modification of the seat.

In a preferred embodiment of the invention, the surface of the seat is configured into cross-hatching (see FIG. 8). In a most preferred embodiment of the invention, the surface of the seat is configured into a sun-dial or clock face structure (see FIG. 7). Both of these embodiments, as well as other surface configurations disclosed herein, promote the collection of particulate matter on the collection site in a predetermined spatial arrangement. The configurations shown in FIGS. 7 and 8 are particularly desirable because the imprint of the surface treatment of the seat 39 may be transferred to the microscope slide and used to locate and identify specific particulate matter, such as a cancer cell, using a coordinate system. It has been found that a greater portion of particulate matter collects in regions on the collection site 36 corresponding to or opposite low areas 75 of the seat 39. Conversely, high spots 76 are regions that correspond to areas where smaller amounts of particulate matter collects on the collection site 36. These regions are imprinted on the microscope slide when the collection site 36 is placed in contact with the slide.

For example, a technician reading a microscope slide according to the present invention may be able to identify and locate a cell of interest by noting that the particular cell can be found at "2 o'clock." Imprinting a microscope slide in such a manner significantly speeds reviewing slides and significantly improves the ability of a technician to find previously identified matter of interest. Included with the invention are one or more structures on the seat surface that provide positive orientation of the particulate matter as it is collected on the collection site and transferred to the microscope slide. For example, a suitable coordinate-identifying structure may be an arrow 71 or the like, as shown in FIG. 7.

In accordance with another embodiment of the invention, the seat 39 and/or lower portion 32 may optionally include a peripheral channel 70 or the like, examples of which are shown in FIGS. 7–11. In a preferred embodiment of the invention, seat 39 slopes slightly outward toward the channel 70. The slight slope of the seat and the channel promote enhanced fluid flow through the housing and decreases the surface tension of the seat, both of which promote the capability of the porous arrangement 35 to disengage from the lower portion 32 of the particulate matter separation housing. This aspect of the invention is another structure that promotes release of the porous arrangement.

Figure 9:
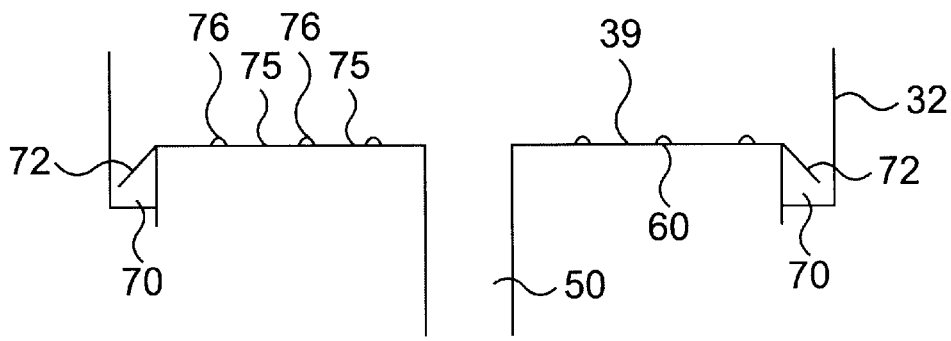
FIG. 9 is a cross section view of the lower portion of the particulate matter separation housing, and shows the optional channel and optional flap.
Figure 10:
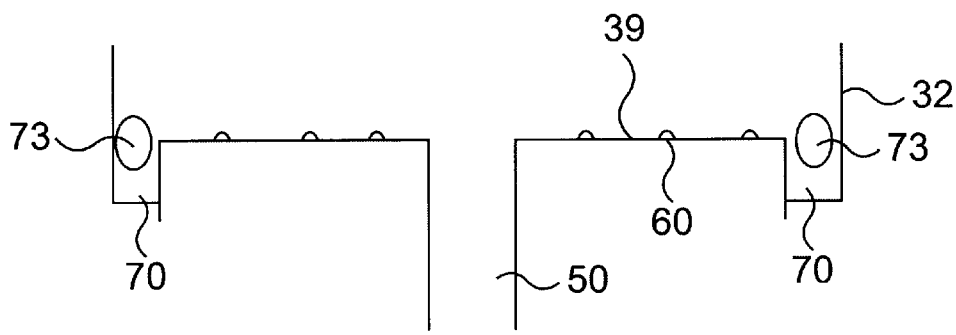
FIG. 10 is a cross section view of the lower portion of the particulate matter separation housing, and shows the optional channel and optional o-ring.
Figure 11:
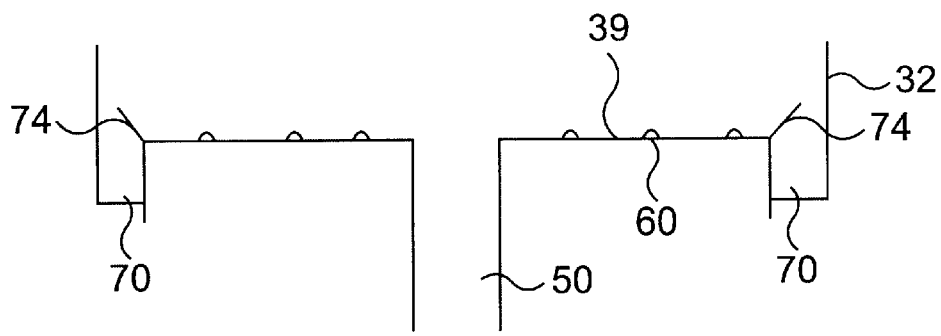
FIG. 11 is a cross section view of the lower portion of the particulate matter separation housing, and shows the optional channel and optional flap.

Additional structures are shown in FIGS. 9–11 that address or are involved with fluid flow through the particulate matter separation housing 30 and also are involved in the release of the porous arrangement 35 from the lower portion 32. FIG. 9 shows a flap 72 that extends downwardly into channel 70 from the lip of seat 39. FIG. 10 shows an o-ring 73 or the like that is positioned in the channel 70, preferably positioned so that a top portion of the o-ring is slightly above the plane of seat 39. This insures that o-ring 73 will engage a portion of porous arrangement 35 when positioned in the lower portion 32. FIG. 11 shows a flap 74 that extends upwardly from an outer portion of seat 39, insuring that flap 74 will engage a portion of porous arrangement 35 when positioned in the lower portion 32. In a preferred embodiment of the invention, flap 72, o-ring 73, and flap 74 are made of a resilient material. The preferred configuration is that shown in FIG. 11.

In accordance with the invention, the particulate matter separation housing 30 defines a porous arrangement chamber which is configured to receive a porous arrangement 35 having a particulate matter collection site 36 adapted to collect particulate matter as fluid containing the particulate matter passes through the chamber.

Figure 3:
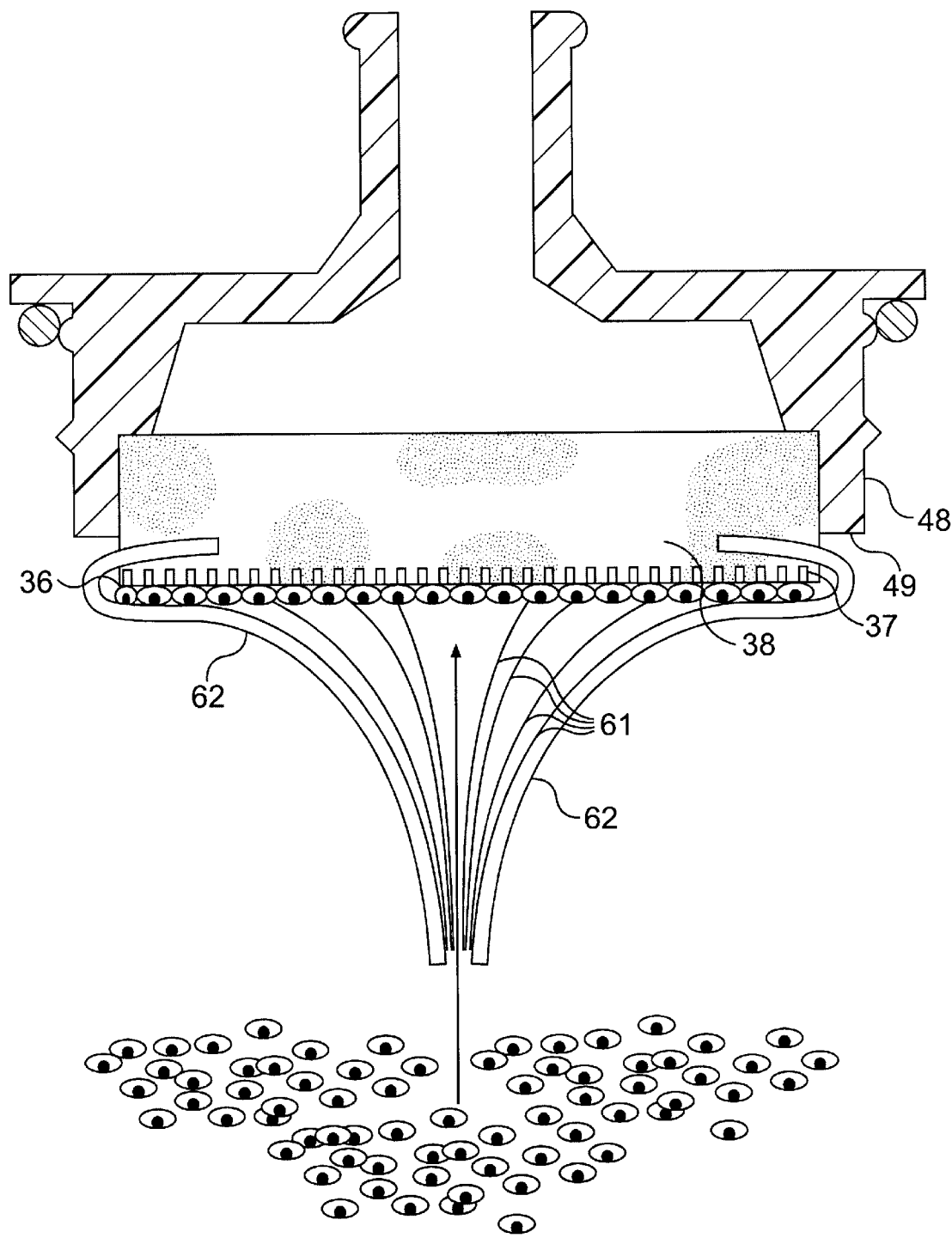
FIG. 3 is a cross section view of the fluid flow paths through the particulate matter separation housing.

Porous arrangement 35 having a collection site 36 adapted to collect particulate matter may be positioned across a fluid flow path, the collection site 36 communicating with hollow tube 50. Referring to FIG. 3, the porous arrangement 35 within the particulate matter separation housing 30 is preferably adapted to define at least one fluid flow path having first and second branches, the first branch 61 extending through the collection site 36 and the second branch 62 bypassing the collection site 36.

In a preferred embodiment, the invention includes a porous arrangement 35 having a first porous medium 37, suitable for preventing the passage of matter therethrough, and a second porous medium 38, suitable for allowing fluid to pass therethrough. The second porous medium may or may not be capable of removing particulate matter from the fluid, a design choice according to the needs of a particular device. In a preferred embodiment, the first porous medium is suitable for capturing or collecting particulate matter, and even more preferably, capturing or collecting solid matter in a uniform or single layer. In a preferred embodiment the a second porous medium 38 is suitable as a support for the first porous medium.

The nature of the material used to make the porous media, the compatibility of the materials chosen for the porous media with one another and with the liquid to be processed are all factors to be considered in selecting a particular material for a porous medium for a given application.

Porous arrangement 35 may include a unitary structure having a first portion of density and/or pore size suitable to prevent the passage of cells threrethrough and a second portion of density and/or pore size suitable for passing the fluid therethrough.

In a preferred embodiment, the porous arrangement includes a first porous medium comprising a porous polycarbonate membrane, suitable for preventing the passage of cells therethrough. The porous arrangement may further include second porous medium comprising a depth filter. The depth filter may be made of polypropylene or high density polyethylene POREX® porous plastics. In a preferred embodiment of the invention, the second porous medium may include a serrated or gear-tooth downstream portion 64, an example of which is illustrated in FIG. 2. It is intended that portion 64 is a structure and configuration that reduces or ameliorates compression of the porous arrangement when it is positioned in the porous arrangement housing.

It should be noted that various types of porous arrangements can be used interchangeably with that of the present embodiment. While a polycarbonate membrane is especially suitable for use in the cytology collection apparatus of the present invention, other porous membranes are also suitable. Exemplary porous membranes are well known in the art, and are disclosed in U.S. Pat. Nos. 5,471,994 and 5,301,685, both hereby incorporated by reference.

The porous membrane preferably has a pore size from about 0.22 microns to about 8 microns, more preferably from about 1 micron to about 6 microns, most preferably about 2 microns, which allows it to trap cells which are more than 3 microns in size. The membrane is suitable to allow fluid flow to pass therethrough while preventing the passage of particulate matter. The second porous medium is suitable for passing fluid therethrough and may also be capable of removing particulate matter from the fluid. The pore size of the second porous medium may range from about 5 microns to about 60 microns, preferably from about 15 microns to about 45 microns, most preferably about 35 microns.

As one skilled in the art will recognize, adjusting the pore size of the porous membrane and the porous depth filter in accordance with the type and/or size of matter to be collected permits the collection of the matter on the collection site 36. In a preferred embodiment of the invention, the pore size is chosen so that a uniform layer of matter, preferably a monolayer of matter, is formed on the collection site. For example, from about 3 $\mu$m to about 40 $\mu$m or more has been shown to be effective, but it is intended that the invention should not be limited to a certain range of pore size.

In a most preferred embodiment of the invention, first porous medium 37 is attached to second porous medium 38 using an adhesive that is soluble in liquid specimen. Such soluble adhesive includes but is not limited to sugar compositions, gels, and the like.

The first porous medium and the second porous medium may be positioned in any fashion that functions as described herein. As one skilled in the art will recognize, the porous arrangement may be variously configured and positioned as needed to achieve a particular result. For example, the first and second porous media may be separate, spaced apart media; the two media can be laminated together; the first medium can be integral with or removably engaged with the second porous medium; or the collection assembly may comprise a zone of higher density which mimics the function of the first porous medium as described above, and a zone of lower density which mimics the function of the second porous medium as described above. Choice of these various configurations is well within the skill of practitioners in the art. Variations on the structure and composition of the porous arrangement will be described in more detail below.

Figure 5:
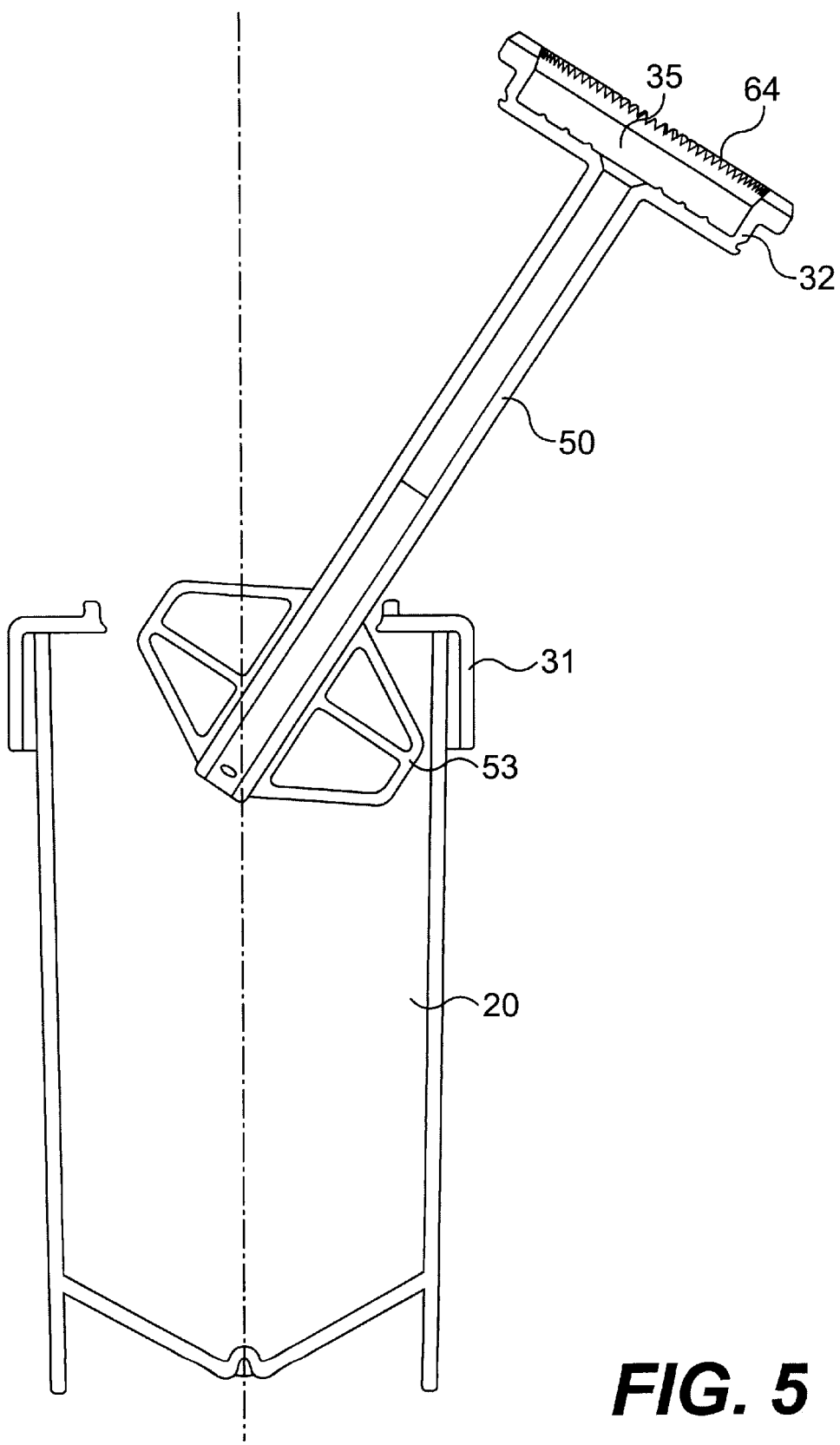
FIG. 5 is a cross section view of a disassembled lower portion, hollow tube, and container.

In another embodiment of the invention, lower portion 32, tube 50, and fins 53 form an integral unit, and may be separated from cover 31 to facilitate removal of the integral structure from container 20. An exemplary structure of this embodiment of the invention is shown in FIG. 5.

Pump

In accordance with the invention, the particulate matter processing apparatus includes a pump 40. In a preferred embodiment of the invention, pump 40 is a syringe or the like for altering differential pressure within the apparatus so that fluid can move from the specimen container 20 through the particulate matter separation housing 30.

In accordance with the present invention, the pump may be variously configured. In a preferred embodiment of the invention, pump 40 includes an end that forms the upper portion 41 of the particulate matter separation housing 30. Upper portion 41 includes a seat 42 or the like configured to engage a downstream portion of porous arrangement 35. In a preferred embodiment of the invention, seat 42 positions porous arrangement 35 in the housing so that porous arrangement 35 does not move during use. In a most preferred embodiment of the invention, seat 42 includes a plurality of projections or posts 43 of a size, shape, and number to position the porous arrangement in the particulate matter separation housing 30, to promote substantially even distribution of pressure against the porous arrangement, and to reduce or prevent compression of the porous arrangement 35 that interferes with fluid flow through the porous arrangement.

In a preferred embodiment of the invention, upper portion 41 removably engages lower portion 32 to form a porous arrangement chamber. Upper portion 41 may engage lower portion 32 in any manner and with any structures that allow upper portion 41 to disengage lower portion 32. In a preferred embodiment of the invention, illustrated in FIG. 2, upper portion 41 includes a downwardly extending side wall 44 having a flange 45 or the like adapted to releasably and/or resiliently engage a shoulder 46 or the like on lower portion 32.

Any suitable pump type device, such as an autovial spunglass filter manufactured by Genex Corporation, could be used. Also included in the scope of the present invention is the use of a flexible, collapsible container, such as a specimen container, which may be squeezed to force fluid through the cytology collection apparatus and into the syringe.

Movement of a fluid through the system may be effected by maintaining a pressure differential between a source of the fluid and a destination for the fluid. Exemplary means of establishing this pressure differential may be by applying pressure to any part of the system on the inlet side of the particulate matter separation housing (e.g., the specimen container); applying a vacuum to any part of the system on the outlet side of the housing (e.g., the syringe); or any form of pump, such as an autovial spunglass filter (manufactured by Genex Corporation); gravity head; or a flexible, collapsible container, such as a specimen container, which may be squeezed to force fluid through the matter collection apparatus and into the syringe. In a preferred embodiment of the invention, a syringe draws fluid from the specimen container through the particulate matter separation housing.

Hollow Tube

In accordance with a preferred embodiment of the present invention, specimen container 20 includes a tube 50 or the like for drawing fluid from the collection chamber 23 into the particulate matter separation housing 30. Typically, tube 50 will be hollow and open or openable at both ends. Tube 50 includes open end 51 near the bottom of the collection chamber 23, and may include one or more apertures 52 into tube 50. Open end 51 and/or apertures 52 permit different fluid layers as well as sediments to be simultaneously tested when the fluid is withdrawn from the collection chamber.

In accordance with another embodiment of the improved invention, hollow tube 50 includes at least one projection or fin 53 or the like, as shown in FIG. 1. In a preferred embodiment of the invention, hollow tube 50 is rotatable and fin 53 stirs the liquid specimen, and in a most preferred embodiment, to disperse cells and/or particulate matter, and/or to disrupt any large particulate matter such as mucoid bodies. In a most preferred embodiment of the invention, hollow tube 50 and lower portion 32 are of unitary construction, and the lower portion 32, tube 50, and fin 53 are movable in relation to the specimen container 20. For example, if the container is rotated, optional fins in the side and/or bottom walls of the container may create concentric movement of the sample in the container, movement that will be disrupted by the presence of fin 53. Alternatively, lower portion 32, tube 50, and fin 53 may be rotated within a stationary container.

Kit

The present invention is also directed to a particulate matter collection and testing kit containing the collection apparatus 10 as an integral unit. As noted in more detail below, a kit may a include at least one specimen container, at least one particulate matter collection assembly, at least one pump, and at least one porous arrangement. A kit according to the invention may also include replacement filters, replacement disposables, and/or other components or solutions typically used during particulate matter testing or examination procedures, e.g., cytological examinations.

Method

The present invention also includes a method for removing particulate matter from a fluid, and for transferring particulate matter, such as cells, to a microscope slide. In contrast to currently available methods, the use of membrane filtration provides a method of depositing cells evenly over a microscope slide with minimal overlap. This allows for clear observation and optimal diagnostic accuracy.

A method includes collecting a fluid sample containing particulate matter in a specimen container 20. The container 20 is then capped with an assembly that includes one or more of the following: cover 31, particulate matter separation housing 30, and pump 40. Pump 40 is then activated to pull fluid from container 20 through particulate matter separation housing 30 into pump 40, e.g., by withdrawing the piston in a syringe.

When the fluid is pulled from the container 20 to the pump 40, fluid will flow through porous arrangement 35 as shown in FIG. 3, so that a monolayer of particulate matter is formed on collection site 36. Once the monolayer of cells is formed, fluid flow is reduced in the center of porous arrangement 35 and increases towards the edges of the porous arrangement. This may be due to the blockage of fluid flow by the collected cells as they form the monolayer on the surface (collection site) 36 of the porous arrangement. When the monolayer has mostly covered the surface of the porous arrangement 35, the flow of fluid bypasses the first porous medium and passes through the extended side area of the second porous medium 38. Thus, the area of the second porous medium extending beyond an end wall 49 of skirt 48 of the upper portion 41 acts as a vent (with low resistance to flow) which prevents cells piling up or collecting in more than a monolayer. Fluid may be passed back and forth through the porous arrangement as many times as desirable.

Pump 40 (and upper portion 41) may then be disconnected from lower portion 32 thereby exposing porous arrangement 35. Once porous arrangement 35 is removed from lower portion 32, easy access is gained to first porous medium 37. Alternatively, removal of upper portion 41 with pump 40 may include removing porous arrangement 35 from lower portion 32.

The first porous medium 37 may then be pressed against a microscope slide to allow particulate matter on the collection site 36 to be transferred as they were collected onto the slide. This allows a cytological examination to be performed on the cells by the practitioner without the interference of the pores in the membrane or delay due to processing requirements.

Since cellular detail is dependent on fixation, it is preferred that cells be fixed immediately after being deposited on the slide. Too long a delay between preparation and fixation may expose the cells to drying, which may be detrimental to the cellular structure. Moreover, air drying artifacts can adversely affect the subsequent staining results. An exception is when the cells are stained with Wright-Giemsa, where air drying is used as the fixation step.

In an another embodiment of the present invention, the monolayer of cells may be fixed directly on the collection site. This may be carried out by first depositing a monolayer of cells on the collection site of the cytology collection apparatus as described above and subsequently passing a solution containing a fixative, such as alcohol or acetone, through the cytology collection apparatus.

Alternative Configurations

The matter collection apparatus or module described above may be used in combination with other suitable filtration or treatment devices. Exemplary devices include other debris and/or assay devices or modules which may be attached to apparatus 10. Typically, these additional modules will include a housing having an inlet and an outlet, and will include a filtration, assay, or detection element positioned across the fluid flow path in the housing. For example, the apparatus may comprise a housing including inlet and outlet ports defining a flow path between the inlet and the outlet; a filter positioned across the flow path; and a freely movable chromatography/assay element, such as substrate beads, positioned on the outlet side of the filter. The chromatography/assay element can freely mix with the matter in the fluid, capture the matter, and can then be assayed for the presence of the matter. Suitable devices include those disclosed in U.S. Pat. Nos. 4,953,561; 5,224,489; 5,016,644; 5,139,031; 5,301,685; 5,042,502; and 5,137,031, all incorporated herein by reference.

Included within the scope of the present invention is producing a single slide from a patient sample, producing multiple slides from a single patient sample, or producing multiple slides from multiple patient samples. It is intended that a patient sample may be processed in a single shot, batch, or continuous manner. Additional slides for other stain applications can be easily prepared. Human papilloma virus testing, for example, by newer methods such as immunocytochemistry or in-situ hybridization can be performed on the additional slides. As oncogene products or other immunocytochemical tests are developed, more slides may be necessary. The different fixations that these tests may need can easily be incorporated into the procedure since the preparation does not require the slides to be fixed in only one way.

This same slide preparation procedure can be used for virtually all forms of cytology. Furthermore, the use of completely contained disposable components addresses biohazard concerns. Ultimately, the enhanced presentation of cells, yielding improved cytologic interpretation, may expand the role of cytology by providing more consistent and reliable patient diagnosis.

Also, captured microorganisms can be cultured in culture medium. After a monolayer of cells has been collected in the cytology collection apparatus, fluid may be used to backflush the collection site, thereby transferring any collected microorganisms from the collection site.

In bacteria testing, the first porous medium can be used for culturing with a Qualture device (not shown) to determine the presence of specific bacteria colonies. The Qualture device is a plastic capsule containing a filter membrane and four nutrient pads of dehydrated, selective media.

The Qualture technique is more sensitive than the agar plate method and more rapid in determining a presumptive diagnosis. The device screens, isolates and presumptively diagnoses bacterial isolates in one step most often in 4–6 hours. Tests have demonstrated that recovery from fifty milliliters of fluid is excellent and sensitive.

Although the present invention has been described in terms of a particular preferred embodiments, it is not limited to those embodiments. Alternative embodiments, examples, and modifications which would still be encompassed by the invention may be made by those skilled in the art, particularly in light of the foregoing teachings.

What is claimed is:

1. An apparatus for separating particulate matter from a liquid comprising:

a container having a cover, the cover having an opening;

a particulate matter separation housing engaging the cover and in fluid communication with the container through said opening, the engagement of the housing and the cover permitting unlimited rotation of at least a portion of the housing relative to the cover;

a porous arrangement in said housing suitable for removing particulate matter from the liquid, the porous arrangement having a collection site on which particulate matter is collected; and a pump in fluid communication with said housing for drawing liquid from the container through said housing and through said porous arrangement.

2. An apparatus according to claim 1, wherein said housing comprises separable lower and upper housing portions, the lower housing portion engaging the cover and rotatable relative thereto, and the upper housing portion being in fluid communication with the pump.

3. An apparatus according to claim 2, wherein said lower housing portion comprises a seat which contacts said porous arrangement at said collection site.

4. An apparatus according to claim 3, wherein said lower housing portion is configured to release the porous arrangement when said upper and lower housing portions are separated.

5. An apparatus according to claim 4, wherein said seat is configured to reduce the surface tension of the seat and thereby reduce the ability of the seat to retain the porous arrangement when said housing portions are separated.

6. An apparatus according to claim 5, wherein the surface of the seat is sloped in the radial direction from the center thereof.

7. An apparatus according to claim 6, wherein said lower housing portion comprises a peripheral channel surrounding said seat.

8. An apparatus according to claim 3, wherein said seat has projections which contact said porous arrangement.

9. An apparatus according to claim 8, wherein said projections are arranged in a predetermined pattern.

10. An apparatus according to claim 9, wherein said predetermined pattern is selected from the group consisting of concentric circles, concentric squares, concentric rectangles, sun-dial, clock face, grid and cross-hatching.

11. An apparatus according to claim 8, wherein said projections are selected from the group consisting of ribs, nubs, protruberances, granulations and combinations thereof.

12. An apparatus according to claim 4, wherein said lower housing portion comprises a peripheral channel surrounding said seat, and a resilient member positioned in said channel and contacting said porous arrangement.

13. An apparatus according to claim 12, wherein said resilient member is an O-ring or a flap.

14. An apparatus according to claim 4, wherein said upper housing portion engages said porous arrangement and is configured to retain said porous arrangement when said upper and lower housing portions are separated.

15. An apparatus according to claim 14, wherein said upper housing portion comprises a seat having posts which engage said porous arrangement.

16. An apparatus according to claim 3, wherein said seat has a surface configured to distribute particulate matter on the collection site in a predetermined spatial distribution.

17. An apparatus according to claim 3, wherein said seat has a textured surface which contacts said porous arrangement.

18. An apparatus according to claim 2, wherein the engagement of said lower housing portion and said cover which permits unlimited relative rotation thereof comprises a tongue and groove arrangement.

19. An apparatus according to claim 18, wherein said lower housing portion is received within the opening in said cover.

20. An apparatus according to claim 2, wherein said upper housing portion has a downwardly facing seat, and said lower housing portion has a side wall with a serrated portion that engages said downwardly facing seat.

21. An apparatus for separating particulate matter from a liquid comprising:

a container having a cover, the cover having an opening;

a particulate matter separation housing in fluid communication with the container, said housing comprising separable upper and lower housing portions, the lower housing portion engaging the cover so as to permit unlimited rotation of the lower housing portion relative to the cover;

a tube supported by the lower housing portion and extending through said opening into the container, the tube having at least one dispersing element for dispersing particulate matter in the liquid when said lower housing portion is rotated relative to the cover;

a porous arrangement in said housing suitable for removing particulate matter from the liquid, the porous arrangement having a collection site on which particulate matter is collected; and a pump in fluid communication with said upper housing portion for drawing liquid from the container through said tube, through said housing and through said porous arrangement.

22. An apparatus according to claim 21, wherein said lower housing portion and said cover are rotatably engaged through a tongue and groove arrangement.

23. An apparatus according to claim 22, wherein said lower housing portion is received within the opening in said cover.

24. An apparatus according to claim 23, wherein said opening has a radially inwardly facing groove, and said lower housing portion has a radially outwardly facing tongue received in said groove.

25. An apparatus for separating particulate matter from a liquid comprising:

a container having a cover, the cover having an opening;

a particulate matter separation housing in fluid communication with the container, said housing comprising separable upper and lower housing portions, the lower housing portion engaging the cover so as to permit unlimited rotation of the lower housing portion relative to cover;

a tube supported by the lower housing portion and extending through said opening into the container;

a porous arrangement in said housing suitable for removing particulate matter from the liquid, the porous arrangement having a collection site on which particulate matter is collected; and a pump in fluid communication with said upper housing portion for drawing liquid from the container through said tube, through said housing and through said porous arrangement, wherein said lower housing portion comprises a seat which contacts said porous arrangement at said collection site, and said lower housing portion is configured to release the porous arrangement when said upper and lower housing portions are separated, and wherein said upper housing portion engages said porous arrangement and is configured to retain said porous arrangement when said upper and lower housing portions are separated.

26. An apparatus according to claim 25, wherein said lower housing portion and said cover are rotatably engaged through a tongue and groove arrangement.

27. An apparatus according to claim 26, wherein said lower housing portion is received within the opening in said cover.

28. An apparatus according to claim 25, wherein said seat is configured to reduce the surface tension of the seat and thereby reduce the ability of the seat to retain the porous arrangement when said housing portions are separated.

29. An apparatus according to claim 25, wherein said seat has a surface configured to distribute particulate matter on the collection site in a predetermined spatial distribution.

30. An apparatus according to claim 28, wherein the tube has at least one dispersing element for dispersing particulate matter in the liquid in the container when said lower housing portion is rotated relative to the cover.

31. A method of separating particulate matter from a liquid containing the particulate matter using the apparatus of claim 28, comprising:

activating the pump to pull liquid containing particulate matter from the container upwardly through the tube, pass the liquid containing particulate matter through the porous arrangement in the housing and collect a substantially uniform layer of said particulate matter on the collection site of said porous arrangement; and separating said upper and lower housing portions while retaining said porous arrangement in said upper housing portion.

32. A method according to claim 31, further comprising transferring at least a portion of the particulate matter on said collection site to a slide.

* * * * *